United States Patent [19]

Saeki et al.

[11] Patent Number: 4,908,479

[45] Date of Patent: Mar. 13, 1990

[54] N-PHENYL-2,2,6,6-TETRAHALOCYCLOHEXANEIMINE

[75] Inventors: Takeaki Saeki, Fujiidera; Hideo Ishikawa, Mino; Tunehei Oki, Osaka, all of Japan

[73] Assignee: Osaka Yuki Kagaku Kogyo Kabushiki Kaisha, Osaka, Japan

[21] Appl. No.: 228,134

[22] Filed: Aug. 3, 1988

[30] Foreign Application Priority Data

Oct. 30, 1987 [JP] Japan ............................ 62-277204
Oct. 30, 1987 [JP] Japan ............................ 62-277205
Oct. 30, 1987 [JP] Japan ............................ 62-277206

[51] Int. Cl.$^4$ .................................. C07C 119/14
[52] U.S. Cl. ................................ 564/277; 568/376
[58] Field of Search ...................... 564/277; 568/376

[56] References Cited

U.S. PATENT DOCUMENTS

| | | | |
|---|---|---|---|
| 2,674,572 | 4/1952 | Gundel et al. | 568/376 X |
| 2,972,563 | 2/1961 | Richter | 564/277 X |
| 3,094,560 | 6/1963 | Luvisi et al. | 564/277 X |
| 3,558,690 | 1/1971 | Sallman et al. | |
| 3,804,877 | 4/1974 | Sallman et al. | |
| 3,895,063 | 7/1975 | Sallman et al. | |

*Primary Examiner*—Robert V. Hines
*Attorney, Agent, or Firm*—Armstrong, Nikaido, Marmelstein, Kubovcik & Murray

[57] ABSTRACT

A process for preparing a 2,2,6,6-tetrahalocyclohexanimine derivative (I) which comprises reacting a 2,2,6,6-tetrahalocyclohexanone with a primary amine or ammonia in the presence of a Lewis acid, a process for preparing a 2,6-dihaloaniline derivative (II) which comprises subjecting the 2,2,6,6-tetrahalocyclohexaneimine derivative (I) to dehydrohalogenation in the presence or absence of a catalyst, and an N-phenyl-2,2,6,6-tetrahalocyclohexaneimine. According to the process of the present invention, the 2,2,6,6-tetrahalocyclohexaneimine derivative (I) can be prepared from inexpensive starting materials in high yield through a few steps. Also, the 2,6-dihaloaniline derivative (II) can be prepared from inexpensive starting materials in high yield and high purity through a few steps. Further, the N-phenyl-2,2,6,6-tetrahalocyclohexaneimine is very useful in the preparation of N-phenyl-2,6-dihaloaniline.

1 Claim, No Drawings

N-PHENYL-2,2,6,6-TETRAHALOCYCLOHEX-ANEIMINE

BACKGROUND OF THE INVENTION

The present invention relates to a process for preparing 2,2,6,6-tetrahalocyclohexaneimine derivatives having the formula (I):

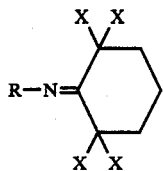

wherein R is a hydrogen atom, a linear or branched alkyl group, or a substituted or unsubstituted aromatic group, and each X is a halogen atom, which are starting materials of 2,6-dihaloaniline derivatives. The 2,6-dihaloaniline derivatives having the formula (II):

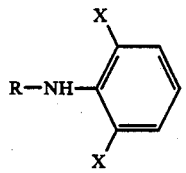

wherein R and X are as defined above, are intermediates of substituted phenylacetic acids suitable for use of an antiphlogistic, analgesic or antipyretic, as shown in Japanese Examined Patent Publication No. 23418/1967. More particularly, the present invention relates to a process for preparing 2,2,6,6-tetrahalocyclohexaneimine derivatives having the formula (I) which comprises subjecting to dehydration condensation of a 2,2,6,6-tetrahalocyclohexanone with a primary amine or ammonia.

Also, the present invention relates to a process for preparing 2,6-dihaloaniline derivatives having the formula (II), and more particularly to a process for preparing 2,6-dihaloaniline derivatives (II) which comprises subjecting to dehydrohalogenation of the 2,2,6,6-tetrahalocyclohexaneimine derivatives (I).

Further, the present invention relates to an N-phenyl-2,2,6,6-tetrahalocyclohexaneimine having the formula (III):

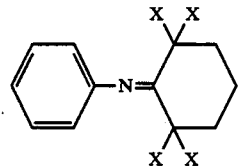

wherein each X ia a halogen atom. The novel compound (III) is a starting material of an N-phenyl-2,6-dihaloaniline which is one of intermediates of substituted phenylacetic acids suitable for use of antiphlogistic, analgesic, antipyretic, and the like.

The 2,2,6,6-tetrahalocyclohexaneimine derivative (I) is especially useful as a starting material of the 2,6-dihaloaniline derivative (II).

Also, the 2,6-dihaloaniline derivative (II) is useful as an intermediate of the substituted phenylacetic acid useful as drugs or agricultural chemicals. Particularly, as disclosed in Japanese Examined Patent Publication No. 23418/1967, the derivative (II) is useful as an intermediate of one of substituted phenylacetic acids, having the formula (IV):

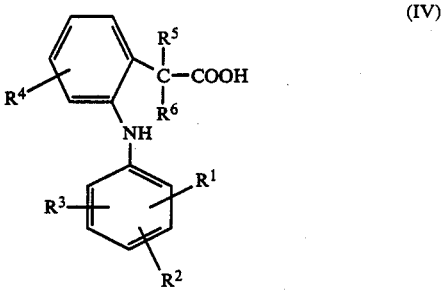

wherein $R^1$ is a lower alkyl group, a lower alkoxyl group, a halogen atom of fluorine, chlorine or bromine, or a trifluoromethyl group, each $R^2$ and $R^3$ is a hydrogen atom, a lower alkyl group, a lower alkoxyl group or a halogen atom of fluorine, chlorine or bromine, $R^4$ is a hydrogen atom, a lower alkyl group, a lower alkoxyl group, a halogen atom of fluorine, chlorine or bromine or a trifluoromethyl group, and each $R^5$ and $R^6$ is a hydrogen atom, a lower alkyl group or a benzyl group.

It has been known that a 2,2,6,6-tetrahalocyclohexanone is reacted with an alcoholate to give a 2-alkoxy-3-halophenol, and also it is dehydrohalogenated with an amine to give a 2,6-dihalophenol. However, it has not been known that the 2,6,6,6-tetrahalocyclohexanone is subjected to dehydration condensation with the amine, e.g. it is reacted with ammonia or a primary amine to produce a ketimine.

On the other hand, the 2,6-dihaloaniline derivative (II) can be prepared by various known processes. For example, Japanese Examined Patent Publication No. 23418/1967 discloses a process for preparing the 2,6-dihaloaniline derivative and a process for preparing a substituted phenylacetic acid therefrom, as shown in the following reaction formulae:

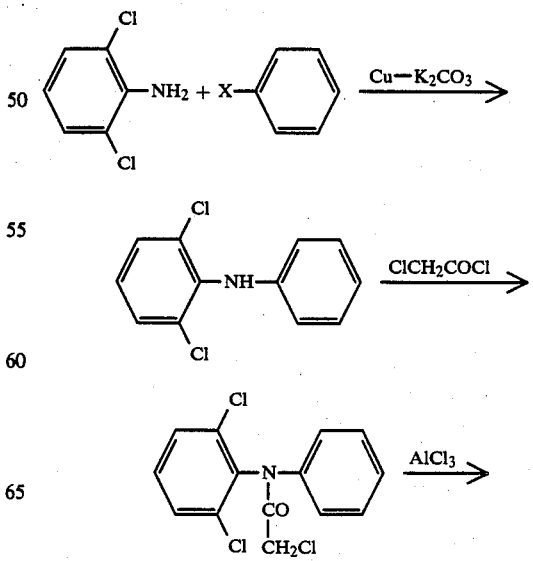

-continued

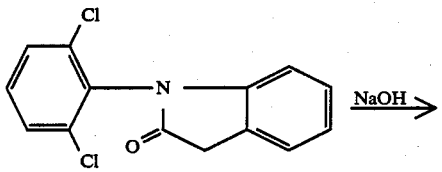

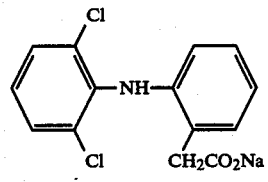

wherein X is bromine atom or iodine atom. In the above reaction formulae, a 2,6-dihaloaniline is produced by halogenating an N-acetylsulfanil chloride to give a 2,6-dihalo-N-acetylsulfanil chloride and hydrolyzing the obtained compound to eliminate acetyl group and chlorosulfonyl group therefrom. Then, the obtained 2,6-dihaloaniline is condensed with a halide such as iodobenzene or bromobenzene according to Ullmann reaction in the presence of copper powder and potassium carbonate at high temperature to give the 2,6-dihaloaniline derivatives.

In the above-mentioned process, for preparing the 2,6-dihaloaniline derivatives, there are some problems that the yield is low or wastes are produced in a large amount since several steps are required for obtaining the 2,6-dihaloaniline; in case of using the iodine compound as the halide for obtaining the 2,6-dihaloaniline derivatives, the cost of products becomes high because the iodine compounds are expensive; in case of using the bromo compound, 2-chloro-6-bromoaniline is generated as a by-product, consequently, very much time and labor are required in order to separate and purify the desired product.

It is an object of the present invention to provide a process for preparing the 2,2,6,6-tetrahalocyclohexaneimine derivative (I) from inexpensive starting materials in high yield through a few steps. The 2,2,6,6-tetrahalocyclohexaneimine derivatives (I) are very useful as starting materials for obtaining the 2,6-dihaloaniline derivatives (II) inexpensively in high purity.

It is a further object of the present invention is to provide a process for preparing the 2,6-dihaloaniline derivative (II) from inexpensive starting materials in high yield and high purity through a few steps. The 2,6-dihaloaniline derivatives (II) are very useful as intermediates of the substituted phenylacetic acid useful as drugs or agricultural chemicals.

The N-phenyl-2,6-dihaloaniline, for instance, N-phenyl-2,6-dichloroaniline, is prepared by the following reaction formula, as disclosed in Japanese Examined Patent Publication No. 23418/1967.

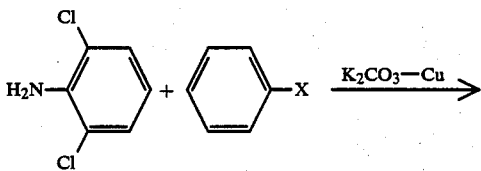

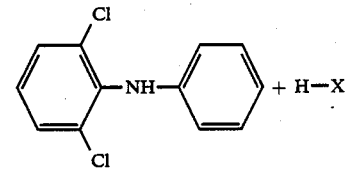

wherein X is bromine atom or iodine atom. The 2,6-dichloroaniline is condensed with iodobenzene or bromobenzene according to Ullmann reaction in the presence of a catalyst of potassium carbonate copper powder to give N-phenyl-2,6-dichloroaniline. However, the process have defects that the cost of products becomes high because 2,6-dichloroaniline and iodobenzene are expensive, when using the compounds. Also, when using bromobenzene, though bromobenzene is relatively cheap, N-phenyl-2-chloro-6-bromoaniline is generated as a by-product. Consequently, very much time and labor are required for purification of the desired products.

It is a still further object of the present invention is to provide an N-phenyl-2,2,6,6-tetrahalocyclohexaneimine having the formula (III):

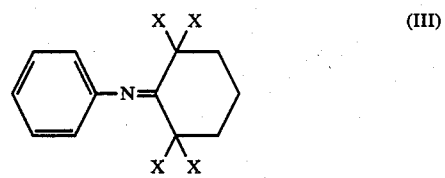

wherein X is a halogen atom. There can be provided from the compound (III) an N-phenyl-2,6-dihaloaniline such as N-phenyl-2,6-dichloroaniline at a low cost in high purity.

These and other objects of the present invention will become apparent from the following description.

SUMMARY OF THE INVENTION

It has now been found that the 2,2,6,6-tetrahalocyclohexaneimine derivative (I) can be efficiently prepared when the 2,2,6,6-tetrahalocyclohexanone is reacted with the primary amine or ammonia in the presence of a Lewis acid such as aluminum chloride, aluminum bromide, zinc chloride, zinc bromide, iron chloride, tin chloride, titanium tetrachloride, boron trifluoride, boron trifluoride etherate, an aluminum alkoxide e.g. aluminum isopropoxide or a titanium alkoxide e.g. tetrabutyl titanate, as a catalyst.

Also, is has now been found that the 2,6-dihaloaniline derivative (II) can be prepared when subjecting the 2,2,6,6-tetrahalocyclohexaneimine derivative (I) to dehydrohalogenation, and particularly when using a solvent such as an aliphatic amide e.g. N,N-dimethylformamide, N,N-dimethylacetamide or hexamethylphosphoramide, an aromatic polar solvent such as chlorobenzene, nitrobenzene, cyanobenzene or anisol, an aliphatic nitrile e.g. acetonitrile or propionitrile, an aprotic polar solvent e.g. dimethyl sulfoxide, the dehydrohalogenation can proceed efficiently.

Further, it has now been found that the N-phenyl-2,2,6,6-tetrahalocyclohexaneimine (III) is a useful novel intermediate for obtaining inexpensively the N-phenyl-2,6-dihaloaniline in high purity.

That is, in accordance with the present invention, there is provided a process for preparing a 2,2,6,6-tetrahalocyclohexaneimine derivative having the formula (I):

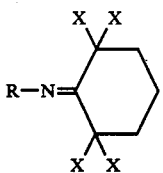

wherein R is a hydrogen atom, a linear or branched alkyl group, or a substituted or unsubstituted aromatic group, and each X is a halogen atom; which comprises reacting a 2,2,6,6-tetrahalocyclohexanone with a primary amine or ammonia in the presence of a Lewis acid.

Also, in accordance with the present invention, there is provided a process for preparing a 2,6-dihaloaniline derivative having the formula (II):

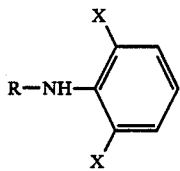

wherein R and X are as defined above; which comprises subjecting the 2,2,6,6-tetrahalocyclohexaneimine derivative (I) to dehydrohalogenation.

Further, in accordance with the present invention, there is provided an N-phenyl-2,2,6,6-tetrahalocyclohexaneimine having the formula (III):

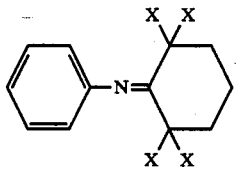

wherein X is as defined above.

DETAILED DESCRIPTION

In the present invention, the 2,2,6,6-tetrahalocyclohexaneimine derivative (I) is prepared as shown by the following reaction formula:

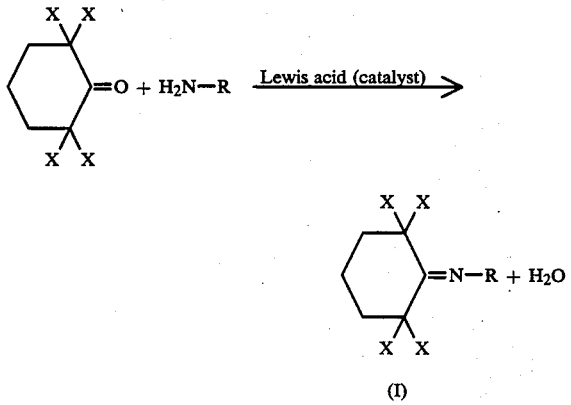

wherein R is a hydrogen atom, a linear or branched alkyl group, or a substituted or unsubstituted aromatic group, and each X is a halogen atom. As shown above, the 2,2,6,6-tetrahalocyclohexaneimine derivative (I) can be prepared by subjecting to dehydration condensation of a 2,2,6,6-tetrahalocyclohexanone with a primary amine or ammonia in the presence of a Lewis acid as a catalyst. The 2,2,6,6-tetrahalocyclohexanone can be easily obtained by halogenation of cyclohexanone. All starting materials, the 2,2,6,6-tetrahalocyclohexanone and the primary amine or ammonia are inexpensive and are easily obtained. As the halogen atom in the 2,2,6,6-tetrahalocyclohexanone, fluorine atom, chlorine atom, bromine atom and iodine atom are preferable.

Any primary amines can be used in the above dehydration condensation so long as the amine does not have a group active to the Lewis acid, such as hydroxyl group. Ammonia can be used in the state of gas or liquid. Examples of the primary amines are, for instance, a linear alkylamine such as methylamine or butylamine, a branched alkylamine such as isopropylamine, an unsubstituted aromatic amine such as aniline or naphthylamine, a substituted aromatic amine such as 2-methoxycarbonylmethylaniline or 2-methylaniline, and the like.

It is preferable that the amount of ammonia or the primary amine is from 1.0 to 5.0 moles per mole of the 2,2,6,6-tetrahalocyclohexanone. When the amount of the ammonia or the primary amine is less than 1.0 mole, the yield of 2,2,6,6-tetrahalocyclohexaneimine derivative is lowered, and when the amount is more than 5.0 moles, which is disadvantageous in the cost.

As the Lewis acid used as the catalyst in the dehydration condensation, there are exemplified, for instance, a metal halide, a metal alkoxide such as an aluminum alkoxide or a titanium alkoxide, and the like. Typical examples of the Lewis acids are, for instance, titanium tetrachloride, aluminum chloride, aluminum bromide, zinc chloride, zinc bromide, iron chloride, tin chloride, boron trifluoride, boron trifluoride etherate, aluminum isopropoxide, tetrabutyl titanate, and the like.

The Lewis acid is an important factor in the dehydration condensation of the present invention. It is preferable that the amount of the Lewis acid is from 0.25 to 2.0 moles per mole of the 2,2,6,6-tetrahalocyclohexanone. When the amount of the Lewis acid is less than 0.25 mole, the yield of 2,2,6,6-tetrahalocyclohexaneimine derivative (I) is remarkably lowered, and when the amount is more than 2.0 moles, there is a tendency that by-products are produced in a large amount. It is more preferable that the amount of the Lewis acid is from 0.75 to 1.2 moles per mole of the 2,2,6,6-tetrahalocyclohexanone.

It is preferable that the reaction time of the dehydration condensation is from 1 to 10 hours. Also, it is preferable that the reaction is carried out at a temperature of not higher than 150° C. since the side reactions become frequently caused when the reaction temperature exceeds 150° C. It is more preferable that the condensation is carried out at a temperature of $-10°$ to 50° C. from the viewpoint of the yield.

The reaction mechanism of the Lewis acid used as the catalyst in the process for preparing the 2,2,6,6-tetrahalocyclohexaneimine derivative (I) is as shown below:

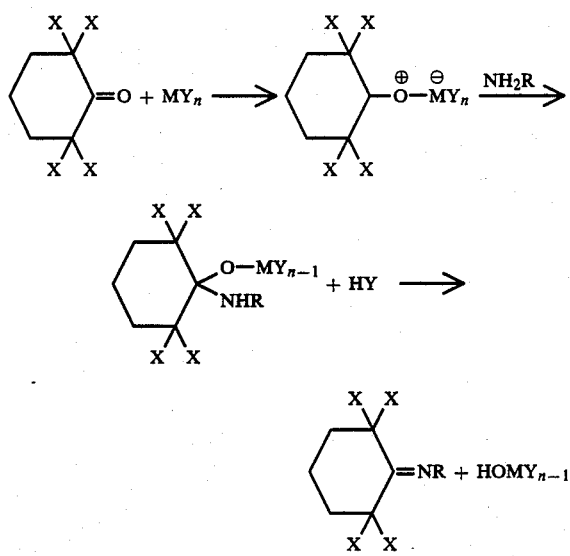

wherein X is a halogen atom, M is aluminum atom, zinc atom, tin atom, iron atom, titanium atom or boron atom, Y is chlorine atom, bromine atom, iodine atom, fluorine atom or an alkoxy group, and n is 2, 3, or 4.

As shown in the reaction formulae, the Lewis acid is coordinated to oxygen atom of carbonyl group in the 2,2,6,6-tetrahalocylohexanone to activate the carbon atom in the carbonyl group. The activated carbon atom is reacted with the nitrogen atom in the primary amine or ammonia, and then the Lewis acid is eliminated as the hydroxide to produce the 2,2,6,6-tetrahalocyclohexaneimine derivative (I).

The carbon atom of the carbonyl group in the 2,2,6,6-tetrahalocyclohexanone is difficult to conduct the nucleophilic reaction, because of large steric hindrance due to the bulky halogen atoms which exist at both next sides of the carbon atom. Accordingly, it has hitherto been known that only cyanide ion can react nucleophilically with the carbon atom of the carbonyl group in the 2,2,6,6-tetrahalocyclohexanone.

In the present invention, in spite of the large steric hindrance, the Lewis acid can activate the carbon atom of the carbonyl group in the 2,2,6,6-tetrahalocyclohexanone and the dehydration condensation of the 2,2,6,6-tetrahalocyclohexanone and the primary amine or ammonia can be efficiently conducted.

In the dehydration condensation, the 2,2,6,6-tetrahalocyclohexanone may be subjected to the reaction without a solvent. Usually, it is preferable that the reaction is carried out in an organic solvent from the viewpoints of inhibiting of occurrence of side reactions and handling.

Any organic solvents can be used in the reaction so long as the solvents are inert to the Lewis acid of the catalyst. Examples of the organic solvents are, for instance, a halogenated hydrocarbon such as carbon tetrachloride, chloroform, methylene chloride or dichloroethane; an aliphatic or alicyclic hydrocarbon such as hexane, pentane or cyclohexane; an aromatic hydrocarbon such as benzene, toluene, xylene or chlorobenzene, and the like.

In the present invention, the 2,2,6,6-tetrahalocyclohexaneimine derivative (I) is prepared by the following procedures. The primary amine or ammonia is added to the 2,2,6,6-tetrahalocyclohexanone in the presence of the Lewis acid, and the mixture is aged at room temperature for 1 to 10 hours to complete the reaction. Then, the catalyst and solvent are removed from the reaction mixture and the desired product is obtained by, for instance, concentration and recrystallization. For instance, in case of using titanium tetrachloride as the catalyst and toluene as the solvent, the reaction mixture is poured into cold water with stirring to hydrolyze the titanium tetrachloride. The solution is separated into a layer of toluene and a layer of water and the toluene layer is taken out. The water layer is extracted with toluene and the extracted layer is added to the toluene layer. The toluene layer is concentrated under reduced pressure to give the crude 2,2,6,6-tetrahalocyclohexaneimine derivative (I). Then, the obtained crude product can, for example, be purified by recrystallization from methanol to give the pure 2,2,6,6-tetrahalocyclohexaneimine derivative (I).

The N-phenyl-2,2,6,6-tetrahalocyclohexane imine, which is a typical example of the 2,2,6,6-tetrahalocyclohexaneimine derivative (I), can be prepared as mentioned below. That is, the tetrahalocyclohexanone is dissolved in the organic solvent, and aniline is added dropwise thereto in the presence of the Lewis acid as the catalyst. It is preferable that the amount of aniline is from 1.0 to 5.0 moles per mol of the tetrahalocyclohexanone. The reaction may be carried out in the absence of the solvent. Usually, it is preferable to carry out the reaction in the organic solvent. The same organic solvent as mentioned above can be used.

Also the same Lewis acids as mentioned above can be used in order to improve the reaction efficiency.

In case that the reaction is carried out by using 2,2,6,6-tetrachlorocyclohexanone, it is preferable that the amount of the catalyst is from 0.25 to 2.0 moles, preferably 0.75 to 1.2 moles, per mole of the 2,2,6,6-tetrachlorocyclohexanone.

It is preferable that the reaction time is from 1 to 10 hours. Also, it is preferable to adjust the dropping velocity of aniline so that the reaction temperature is maintained at a temperature of 5° to 20° C. When the reaction temperature is lower than 5° C., the reaction rate tends to become slow and the yield tends to lower. On the other hand, when the temperature is higher than 20° C., by-products are easily generated, and the yield lowers.

After adding dropwise aniline, the mixture is aged at room temperature for 2 to 5 hours to complete the reaction. Then, in case of using titanium tetrachloride as the catalyst and toluene as the solvent, the reaction mixture is poured into cold water with stirring to hydrolyze titanium tetrachloride, the reaction solution is separated into a layer of toluene and a layer of water, and the toluene layer (the water layer is extracted with toluene and the extracted layer is added to the prior toluene layer) is concentrated under reduced pressure to give a blackish solid. The obtained blackish solid is recrystallized from methanol to give N-phenyl-2,2,6,6-tetrahalocyclohexaneimine as a yellow needle.

That is, the N-phenyl-2,2,6,6-tetrahalocyclohexaneimine (III) can be prepared according to the following reaction formula:

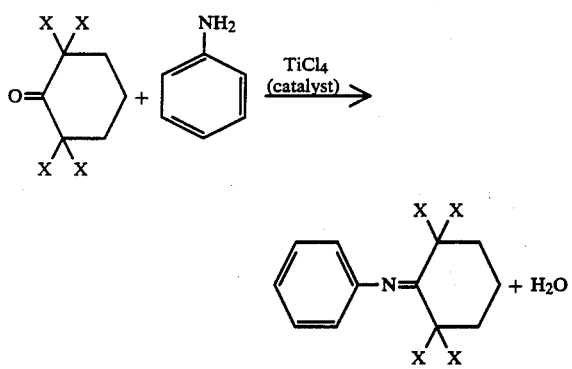

wherein X is as defined above.

From the obtained 2,2,6,6-tetrahalocyclohexaneimine derivative (I), the 2,6-dihaloaniline derivative (II) can be prepared.

The 2,6-dihaloaniline derivative (II) can be prepared by dehydrohalogenating the 2,2,6,6-tetrahalocyclohexaneimine derivative (I) with a catalyst, particularly a base catalyst, or thermal decomposition. The reaction is represented by the following reaction formula:

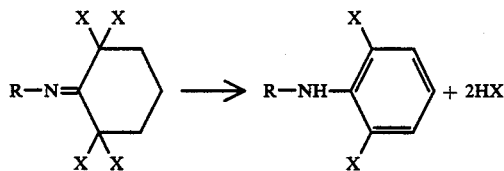

wherein R and X are as defined above.

In the dehydrohalogenation of the 2,2,6,6-tetrahalocyclohexaneimine derivative (I), there can be used the reaction mixture containing the 2,2,6,6-tetrahalocyclohexaneimine derivative (I) obtained in the preparation thereof as it is as well as the isolated and purified product of the 2,2,6,6-tetrahalocyclohexaneimine derivative (I).

Examples of the base catalyst used in the dehydrohalogenation are, for instance, a hydroxide of an alkali metal such as sodium hydroxide, potassium hydroxide or lithium hydroxide; a hydroxide of an alkaline earth metal such as magnesium hydroxide or calcium hydroxide; a carbonate of an alkali metal or alkaline earth metal such as sodium carbonate, potassium carbonate, magnesium carbonate or calcium carbonate; a hydrogencarbonate of an alkali metal such as sodium hydrogencarbonate or potassium hydrogencarbonate; an oxide of an alkali metal or alkaline earth metal such as potassium oxide, magnesium oxide or calcium oxide; organic base such as an amine e.g. triethylamine, pyridine, quinoline, dimethylaniline or aniline; and the like. The catalysts may be used alone or as an admixture thereof. In case of using a suitable base catalyst, the reaction can proceed under milder conditions at high selectivity.

In the dehydrohalogenation, it is preferable that the amount of the catalyst is from 1.0 to 2.4 moles, more preferably from 1.05 to 2.2 moles per mole of the 2,2,6,6-tetrahalocyclohexaneimine derivative (I). It is preferable that the reaction time is from 2 to 8 hours. It is preferable that the reaction temperature is from 50° to 120° C.

The dehydrohalogenation of 2,2,6,6-tetrahalocyclohexaneimine derivative (I) can be efficiently conducted by thermal decomposition even in the absence of the catalyst. In such a case, it is preferable to conduct the reaction at a temperature of 50° to 150° C., more preferably from 90° to 130° C. When the reaction temperature is lower than 50° C., the dehydrohalogenation does not occur. On the other hand, when the reaction temperature is higher than 150° C., side reactions are frequently caused, that is, three halogen atoms are eliminated from the molecule to produce a 2-haloaniline derivative. It is difficult to separate the by-product from the desired product, and the yield is remarkably lowered after separation and purification of the desired product. When the reaction temperature is within the range of 90° to 130° C., the reaction rate is not slow but preferable, and it is difficult to cause the side reactions. In such a case, it can be considered that the dehydrohalogenation is accelerated by catalysis of the 2,2,6,6-tetrahalocyclohexaneimine derivative (I) or the produced 2,6-dihaloaniline derivative (II). That is, because the 2,6-dihaloaniline derivative (II) is an amine and is basic, the produced derivative (II) behaves as an organic basic catalyst.

The 2,2,6,6-tetrahalocyclohexaneimine derivative (I) is dehydrohalogenated with the basic catalyst or with heat to form the 2,6-dihaloaniline derivative (II) through a quinone structure by prototropy.

It is preferable to conduct the dehydrohalogenation in a non-water system because the 2,2,6,6-tetrahalocyclohexaneimine derivative (I) has a structure sterically strained and is easily hydrolyzed in the presence of water. However, in case of using the solvent in the reaction, it is preferred to use a polar solvent since the dehydrohalogenation is easily carried out. It is necessary to thoroughly dry the solvent in order to prevent hydrolysis.

The solvent is a very important factor in the dehydrohalogenation. Examples of the solvents are, for instance, an aliphatic amide such as N,N-dimethylformamide, N,N-dimethylacetamide or hexamethylphosphoramide; an aromatic plar solvent such as chlorobenzene, nitrobenzene, cyanobenzene or anisol; an aliphatic nitrile such as acetonitrile or propionitrile; an aprotic polar solvent such as dimethyl sulfoxide; and the like. The melted derivative (I) may be dehydrohalogenated without the solvent. The reaction is usually carried out in the organic solvent in order to easily control the reaction temperature, and improve the selectivity and the yield.

According to the present invention, the 2,2,6,6-tetrahalocyclohexaneimine derivative (I), which can be converted into the 2,6-dihaloaniline derivative (II) easily and in high purity, can be prepared from the inexpensive starting materials through a few steps in high yield.

Particularly, the N-phenyl-2,2,6,6-tetrahalocyclohexaneimine (III) which is one of embodiments of the 2,2,6,6-tetrahalocyclohexaneimine derivatives (I) can be prepared in high yield from the 2,2,6,6-tetrahalocyclohexanone obtained by halogenation of cyclohexanone and aniline, both of which are inexpensive. Moreover, the N-phenyl-2,2,6,6-tetrahalocyclohexaneimine is easily dehydrohalogenated with the base or heat to form the N-phenyl-2,6-dihaloaniline in high yield and in high purity. Consequently, it can provide the N-phenyl-2,6-dihaloaniline having high purity at low cost.

Also, according to the process of the present invention, the 2,6-dihaloaniline derivative (II), which is very useful as the intermediate of the substituted phenylacetic acid suitable for use as drugs or agricultural chemicals, can be prepared from inexpensive starting materials through a few steps in high yield and high purity.

The present invention is more specifically described and explained by means of the following Examples in which all % are by weight unless otherwise noted. It is to be understood that the present invention is not limited to the Examples, and various changes and modifications may be made in the invention without departing from the spirit and scope thereof.

EXAMPLE 1

A 1 l glass reactor was charged with 90 g (0.39 mole) of 2,2,6,6-tetrachlorocyclohexanone, 200 g of toluene and 81 g (0.43 mole) of titanium tetrachloride, and the mixture was cooled to 5° C. in an ice bath. To the mixture was gradually added dropwise 145 g (1.56 moles) of aniline with stirring. During addition of aniline, the dropping velocity of aniline was adjusted so that the reaction temperature was kept at 5° to 20° C. After dropping aniline, the mixture was aged at room temperature for 2 hours to complete the reaction. The reaction mixture was poured into 300 g of cold water (10° C.) with stirring and titanium tetrachloride was hydrolyzed. The mixture was separated into a layer of toluene and a layer of water. The water layer was extracted twice with toluene and the extracted layer was added to the toluene layer. The obtained toluene layer was concentrated under reduced pressure to give 120 g of a black solid. The obtained black solid was recrystallized from methanol to give 108 g of N-phenyl-2,2,6,6-tetrachlorocyclohexaneimine as yellow needles [yield: 89.6%, melting point (mp): from 71.8° to 72.6° C.]. With respect to the obtained N-phenyl-2,2,6,6-tetrachlorocyclohexaneimine, $^1$H-nuclear magnetic resonance analysis ($^1$H-NMR analysis), infrared spectroscopic analysis (IR analysis) and elementary analysis were conducted. The results are shown as below.

$^1$H-NMR [solvent: CHCl$_3$, internal standard: tetramethyl silane (TMS)]: δ ppm: 7.27 (5H, m,

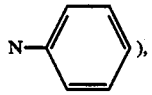

2.85 (4H, t, CH$_2$ at the 3-position and 5-position), 2.10 (2H, q, CH$_2$ at the 4-position).

IR (KBr tablet): $\nu$N=C: 1665 (cm$^{-1}$).

|  | Elementary analysis | | | |
|---|---|---|---|---|
|  | C | H | N | Cl |
| Found (%): | 46.29 | 3.47 | 4.51 | 45.38 |
| Calcd. (%): | 46.34 | 3.57 | 4.50 | 45.59 |

EXAMPLE 2

The procedure of Example 1 was repeated except that the reaction temperature was changed to 30° to 40° C. instead of 5° to 20° C. to give 101 g of N-phenyl-2,2,6,6-tetrachlorocyclohexaneimine (yield: 83.7% mp: from 71.8° to 72.6° C.). With respect to the obtained N-phenyl-2,2,6,6-tetrachlorocyclohexaneimine, $^1$H-NMR analysis, IR analysis and elementary analysis were conducted in the same manner as in Example 1. The obtained results were the same results as in Example 1.

EXAMPLE 3

The procedure of Example 1 was repeated except that the reaction temperature was changed to 95° to 105° C. instead of 5° to 20° C. to give 75.4 g of N-phenyl-2,2,6,6-tetrachlorocyclohexaneimine (yield: 62.5%, mp: from 71.8° to 72.6° C.). With respect to the obtained N-phenyl-2,2,6,6-tetrachlorocyclohexaneimine, $^1$H-NMR analysis, IR analysis and elementary analysis were conducted in the same manner as in Example 1. The obtained results were the same results as in Example 1.

EXAMPLES 4 TO 9

The procedure of Example 1 was repeated except that 1.56 moles of each amine and ammonia shown in Table 1 was used instead of aniline to give oily 2,2,6,6-tetrachlorocyclohexaneimine derivative. In Examples 4 and 5, gaseous ammonia and methylamine were introduced into the mixture of 2,2,6,6-tetrachlorocyclohexanone, toluene and titanium tetrachloride, respectively. The structural formulae, yields and results of IR analysis of the obtained 2,2,6,6-tetrachlorocyclohexaneimine derivatives (I) are shown in Table 1.

TABLE 1

| Ex. No. | Amine or ammonia | 2,2,6,6-Tetrachlorocyclohexaneimine derivative (I) | Yield (%) | IR (cm$^{-1}$) (NaCl plate) |
|---|---|---|---|---|
| 4 | NH$_3$ (gas) | (Cl, Cl, =NH, Cl, Cl structure) | 82 | $\nu_{N=C}$1660 $\nu_{NH}$3320 |
| 5 | CH$_3$NH$_2$ (gas) | (Cl, Cl, =N—CH$_3$, Cl, Cl structure) | 85 | $\nu_{N=C}$1660 |

TABLE 1-continued

| Ex. No. | Amine or ammonia | 2,2,6,6-Tetrachlorocyclo-hexaneimine derivative (I) | Yield (%) | IR (cm$^{-1}$) (NaCl plate) |
|---|---|---|---|---|
| 6 | iso-C$_3$H$_7$NH$_2$ | 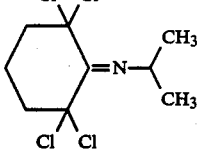 | 86 | $\nu_{N=C}$1660 |
| 7 | 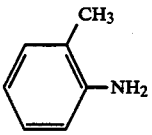 | 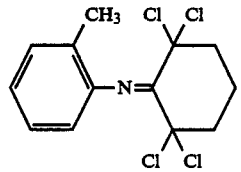 | 90 | $\nu_{N=C}$1665 |
| 8 | 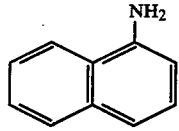 | 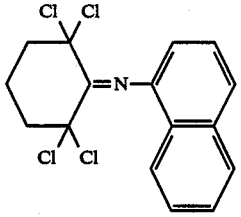 | 65 | $\nu_{N=C}$1665 |
| 9 | 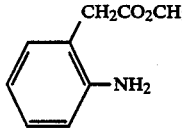 | 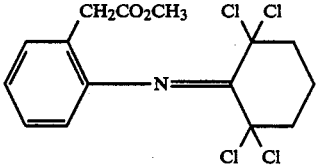 | 72 | $\nu_{N=C}$1665 $\nu_{C=O}$1725 |

EXAMPLES 10 TO 12

The procedure of Example 1 was repeated except that 0.39 mole of each 2,2,6,6-tetrahalocyclohexanone shown in Table 2 was used instead of 2,2,6,6-tetrachlorocyclohexanone to give an N-phenyl-2,2,6,6-tetrahalocyclohexaneimine. The structural formulae of the obtained N-phenyl-2,2,6,6-tetrahalocyclohexaneimines are shown in Table 2 with their yields.

TABLE 2

| Ex. No. | 2,2,6,6-Tetrahalo cyclohexanone | N—phenyl-2,2,6,6-tetra-halocyclohexaneimine | Yield (%) |
|---|---|---|---|
| 10 | 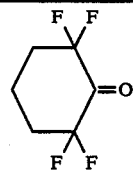 | 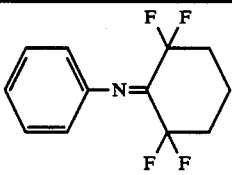 | 91 |
| 11 | 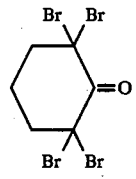 | 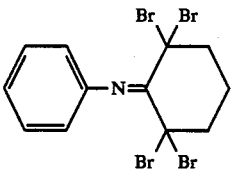 | 63 |
| 12 | 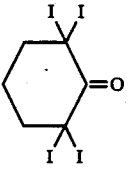 | 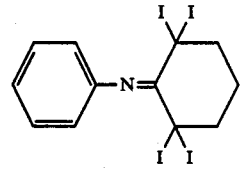 | 26 |

EXAMPLES 13 to 21

The procedure of Example 1 was repeated except that 0.43 mole of each Lewis acid shown in Table 3 was used instead of titanium tetrachloride to give N-phenyl-2,2,6,6-tetrachlorocyclohexaneimine mp: from 71.8° to 72.6° C.). Each yield of them is shown in Table 3. With respect to the obtained N-phenyl-2,2,6,6-tetrachlorocyclohexaneimine, $^1$H-NMR analysis, IR analysis and elementary analysis were conducted in the same manner as in Example 1. The obtained results were the same results as in Example 1.

COMPARATIVE EXAMPLE 1

The procedure of Example 1 was repeated except that titanium tetrachloride was not used. The reaction was not caused, and therefore the desired product, i.e. N-phenyl-2,2,6,6-tetrachlorocyclohexaneimine could not be obtained.

TABLE 3

| Ex. No. | Lewis acid | Yield (%) |
|---|---|---|
| 13 | AlCl$_3$ | 25 |
| 14 | AlBr$_3$ | 21 |
| 15 | ZnCl$_2$ | 36 |
| 16 | SnCl$_4$ | 31 |
| 17 | BF$_3$(C$_2$H$_5$)$_2$O | 53 |
| 18 | Al[OCH(CH$_3$)$_2$]$_3$ | 27 |
| 19 | Ti[O(CH$_2$)$_3$CH$_3$]$_4$ | 75 |
| 20 | FeCl$_3$ | 29 |
| 21 | ZnBR$_2$ | 31 |
| Com. Ex. 1 | — | 0 |

EXAMPLE 22

A 1 l glass reactor was charged with 100 g (0.32 mole) of N-phenyl-2,2,6,6-tetrachlorocyclohexaneimine obtained in Example 1 and 500 g of chlorobenzene, and the mixture was heated in an oil bath with stirring. While keeping the reaction temperature at 100° C., the reaction was continued for 5 hours. After the reaction was completed, the reaction mixture was cooled to 25° C., and washed with 300 g of a 10% aqueous solution of sodium hydroxide. Then, the organic layer was dried with sodium sulfuric anhydride, from which chlorobenzene was distilled away under reduced pressure to give 64.7 g of N-phenyl-2,6-dichloroaniline in the state of a black solid (yield: 85%, mp: 49.5° to 50.7° C.). The obtained N-phenyl-2,6-dichloroaniline had a purity of 92.1% measured by means of gas chromatography.

After N-phenyl-2,6-dichloroaniline was purified by recrystallizing from methanol, $^1$H-NMR analysis, IR analysis and elementary analysis were conducted. The results are shown below.

$^1$H-NMR (solvent: CDCl$_3$, internal standard: TMS): δ ppm: 7.53 to 6.55 (8H, m, benzene ring), 5.83 (1H, S, NH).

IR (KBr tablet): $\nu$NH: 3380 (cm$^{-1}$).

| | Elementary analysis | | | |
|---|---|---|---|---|
| | C | H | N | Cl |
| Found (%): | 60.48 | 3.89 | 5.92 | 29.70 |
| Calcd. (%): | 60.53 | 3.81 | 5.88 | 29.78 |

EXAMPLE 23

The procedure of Example 22 was repeated except that 40 g (0.38 mole) of sodium carbonate was used and that the reaction temperature was kept at 95° C. to give 66.3 g of N-phenyl-2,6-dichloroaniline (yield: 87%, purity: 95.1%). The purity was measured in the same manner as in Example 22. With respect to the obtained N-phenyl-2,6-dichloroaniline, $^1$H-NMR analysis, IR analysis and elementary analysis were conducted in the same manner as in Example 22. The obtained results were the same results as in Example 22.

EXAMPLES 24 TO 32

The procedure of Example 23 was repeated except that 500 g of each solvent shown in Table 4 was used instead of chlorobenzene to give N-phenyl-2,6-dichloroaniline. Each yield and purity of the obtained N-phenyl-2,6-dichloroanilines are shown in Table 4. The purity was measured in the same manner as in Example 22. With respect to the obtained N-phenyl-2,6-dichloroaniline, $^1$H-NMR analysis, IR analysis and elementary analysis were conducted in the same manner as in Example 22. The obtained results were the same results as in Example 22.

TABLE 4

| Ex. No. | Solvent | Yield (%) | Purity (%) |
|---|---|---|---|
| 24 | Nitrobenzene | 88 | 92.7 |
| 25 | Cyanobenzene | 88 | 96.5 |
| 26 | N,N—dimethylformamide | 90 | 99.2 |
| 27 | N,N—dimethylacetamide | 92 | 98.9 |
| 28 | Dimethyl sulfoxide | 89 | 99.5 |
| 29 | Acetonitrile | 75 | 92.8 |
| 30 | Propionitrile | 77 | 93.5 |
| 31 | Hexamethylphosphoramide | 90 | 97.6 |
| 32 | Anisole | 84 | 95.1 |

EXAMPLES 33 TO 47

The procedure of Example 27 was repeated except that each catalyst shown in Table 5 was used in each amount shown in Table 5 instead of 40 g of sodium carbonate to give N-phenyl-2,6-dichloroaniline. Each yield and purity of the obtained N-phenyl-2,6-dichloroaniline are shown in Table 5. The purity was measured in the same manner as in Example 22. With respect to the obtained N-phenyl-2,6-dichloroaniline, $^1$H-NMR analysis, IR analysis and elementary analysis were conducted in the same manner as in Example 22. The obtained results were the same results as in Example 22.

TABLE 5

| Ex. No. | Catalyst | Amount of the catalyst (g) | Amount of the catalyst (mole) | Yield (%) | Purity (%) |
|---|---|---|---|---|---|
| 33 | NaOH | 30 | 0.76 | 80 | 94.7 |
| 34 | KOH | 43 | 0.76 | 81 | 94.2 |
| 35 | Ca(OH)$_2$ | 29 | 0.38 | 87 | 96.5 |
| 36 | Mg(OH)$_2$ | 22 | 0.38 | 88 | 97.8 |
| 37 | NaHCO$_3$ | 64 | 0.76 | 95 | 97.5 |
| 38 | K$_2$CO$_3$ | 52 | 0.38 | 90 | 97.2 |
| 39 | KHCO$_3$ | 76 | 0.76 | 95 | 97.3 |
| 40 | MgCO$_3$ | 32 | 0.38 | 97 | 97.2 |
| 41 | CaCO$_3$ | 38 | 0.38 | 95 | 98.3 |
| 42 | MgO | 15 | 0.38 | 98 | 99.5 |
| 43 | Pyridine | 60 | 0.76 | 90 | 98.1 |
| 44 | Triethylamine | 77 | 0.76 | 91 | 98.6 |
| 45 | Dimethylaniline | 92 | 0.76 | 90 | 98.4 |
| 46 | Aniline | 71 | 0.76 | 78 | 97.2 |
| 47 | Quinoline | 98 | 0.76 | 89 | 98.0 |

EXAMPLES 48 TO 52

The procedure of Example 22 was repeated except that the reaction temperature was changed to each temperature shown in Table 6 instead of 100° C. to give N-phenyl-2,6-dichloroaniline. Each yield and purity of the obtained N-phenyl-2,6-dichloroaniline are shown in Table 6. The purity was measured in the same manner as in Example 22. With respect to the obtained N-phenyl-2,6-dichloroaniline, $^1$H-NMR analysis, IR analysis and elementary analysis were conducted in the same manner as in Example 22. The obtained results were the same results as in Example 22.

TABLE 6

| Ex. No. | Reaction temperature (°C.) | Yield (%) | Purity (%) |
|---|---|---|---|
| 48 | 20 | 1.2 | 97.8 |
| 49 | 50 | 62 | 95.7 |
| 50 | 80 | 80 | 95.1 |
| 51 | 130 | 84 | 89.9 |
| 52 | 150 | 76 | 85.1 |

EXAMPLES 53 TO 57

The procedure of Example 22 was repeated except that each of 2,2,6,6-tetrahalocyclohexaneimine derivatives (I) obtained in Examples 10, 11, 12, 4, 5, 6 and 9 was used instead of N-phenyl-2,2,6,6-tetrachlorocyclohexaneimine to give each of 2,6-dihaloaniline derivatives (II). The structural formulae, yields and purities of the obtained 2,6-dihaloaniline derivative (II) are shown in Table 7. The purity was measured in the same manner as in Example 22.

In addition to the ingredients used in the Examples, other ingredients can be used in the Examples as set forth in the specification to obtain substantially the same results.

What we claim is:

1. An N-phenyl-2,2,6,6-tetrahalocyclohexane imine having the formula (III):

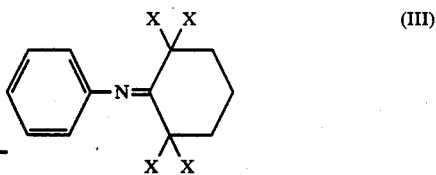

wherein each X is a halogen atom.

* * * * *

TABLE 7

| Ex. No. | 2,2,6,6-Tetrahalo-cyclohexaneimine derivative (I) | 2,6-Dihalo-aniline derivative (II) | Yield (%) | Purity (%) |
|---|---|---|---|---|
| 53 | (F,F,F,F) | (F,F) | 83 | 95.7 |
| 54 | (Br,Br,Br,Br) | (Br,Br) | 73 | 96.2 |
| 55 | (I,I,I,I) | (I,I) | 62 | 93.9 |
| 56 | (Cl,Cl,Cl,Cl) NH | (Cl,Cl) NH2 | 87 | 97.9 |
| 57 | (Cl,Cl,Cl,Cl) with CH3OCOCH2 | (Cl,Cl) with CH3OCOCH2 | 89 | 98.7 |
| 58 | CH3—N= (Cl,Cl,Cl,Cl) | CH3—NH (Cl,Cl) | 82 | 93.3 |
| 59 | (CH3)2CH—N= (Cl,Cl,Cl,Cl) | (CH3)2CHNH (Cl,Cl) | 78 | 94.5 |